(12) United States Patent
Gonzalez

(10) Patent No.: US 9,996,938 B2
(45) Date of Patent: *Jun. 12, 2018

(54) METHODS AND SYSTEMS FOR CORNEAL TOPOGRAPHY, BLINK DETECTION AND LASER EYE SURGERY

(71) Applicant: OPTIMEDICA CORPORATION, Santa Ana, CA (US)

(72) Inventor: Javier G. Gonzalez, Palo Alto, CA (US)

(73) Assignee: Optimedica Corporation, Santa Ana, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/662,203

(22) Filed: Jul. 27, 2017

(65) Prior Publication Data

US 2017/0323450 A1    Nov. 9, 2017

Related U.S. Application Data

(63) Continuation of application No. 14/866,418, filed on Sep. 25, 2015, now Pat. No. 9,721,351.
(Continued)

(51) Int. Cl.
*G06K 9/00* (2006.01)
*G06T 7/20* (2017.01)
(Continued)

(52) U.S. Cl.
CPC ............ *G06T 7/20* (2013.01); *A61B 3/103* (2013.01); *A61B 3/107* (2013.01); *A61B 3/145* (2013.01);
(Continued)

(58) Field of Classification Search
CPC ............... A61B 3/00; G06T 7/00; G06K 9/00
(Continued)

(56) References Cited

U.S. PATENT DOCUMENTS 5,459,570 A   10/1995   Swanson et al.
5,526,072 A    6/1996   El Hage
(Continued)

FOREIGN PATENT DOCUMENTS

| EP | 1700567 A1 | 9/2006 |
|---|---|---|
| WO | 2006090217 A1 | 8/2006 |
| WO | 2011163507 A2 | 12/2011 |

OTHER PUBLICATIONS

International Search Report and Written Opinion for Application No. PCT/US2015/052394, dated Dec. 23, 2015, 14 pages.

*Primary Examiner* — Abolfazl Tabatabai
(74) *Attorney, Agent, or Firm* — Johnson & Johnson Surgical Vision, Inc.

(57) ABSTRACT

A method of blink detection in a laser eye surgical system includes providing a topography measurement structure having a geometric marker. The method includes bringing the topography measurement structure into a position proximal to an eye such that light traveling from the geometric marker is capable of reflecting off a refractive structure of the eye of the patient, and also detecting the light reflected from the structure of the eye for a predetermined time period while the topography measurement structure is at the proximal position. The method further includes converting the light reflected from the surface of the eye into image data and analyzing the image data to determine whether light reflected from the geometric marker is present is in the reflected light, wherein if the geometric marker is determined not to be present, the patient is identified as having blinked during the predetermined time.

20 Claims, 12 Drawing Sheets

Related U.S. Application Data

(60) Provisional application No. 62/055,429, filed on Sep. 25, 2014.

(51) Int. Cl.
| | | |
|---|---|---|
| *G06T 7/70* | (2017.01) | |
| *G06K 9/46* | (2006.01) | |
| *A61B 3/14* | (2006.01) | |
| *G06T 7/00* | (2017.01) | |
| *A61B 3/103* | (2006.01) | |
| *A61B 3/107* | (2006.01) | |
| *G01N 23/207* | (2018.01) | |
| *G01V 3/38* | (2006.01) | |
| *A61F 9/008* | (2006.01) | |

(52) U.S. Cl.
CPC .......... *A61F 9/008* (2013.01); *G06K 9/4633* (2013.01); *G06T 7/0012* (2013.01); *G06T 7/70* (2017.01); *A61F 2009/00846* (2013.01); *A61F 2009/00882* (2013.01); *G06T 2207/20061* (2013.01); *G06T 2207/30041* (2013.01); *G06T 2207/30204* (2013.01)

(58) Field of Classification Search
USPC ........ 382/103, 107, 236; 348/169, 170, 171, 348/172, 352
See application file for complete search history.

(56) References Cited

U.S. PATENT DOCUMENTS

| | | | |
|---|---|---|---|
| 5,720,894 A | 2/1998 | Neev et al. | |
| 5,748,352 A | 5/1998 | Hattori | |
| 5,748,898 A | 5/1998 | Ueda | |
| 5,957,915 A | 9/1999 | Trost | |
| 5,984,916 A | 11/1999 | Lai | |
| 6,019,472 A | 2/2000 | Koester et al. | |
| 6,053,613 A * | 4/2000 | Wei | A61B 3/1005 351/205 |
| 6,111,645 A | 8/2000 | Tearney et al. | |
| 6,454,761 B1 | 9/2002 | Freedman | |
| 7,655,002 B2 * | 2/2010 | Myers | A61F 9/008 606/10 |
| 7,717,907 B2 * | 5/2010 | Ruiz | A61F 9/008 128/898 |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,414,564 B2 | 4/2013 | Goldshleger et al. | |
| 8,518,026 B2 | 8/2013 | Culbertson et al. | |
| 9,721,351 B2 * | 8/2017 | Gonzalez | G06T 7/20 |
| 2008/0281303 A1 | 11/2008 | Culbertson et al. | |
| 2010/0274228 A1 | 10/2010 | Mrochen et al. | |
| 2011/0190739 A1 | 8/2011 | Frey et al. | |
| 2011/0319873 A1 | 12/2011 | Raksi et al. | |
| 2011/0319875 A1 | 12/2011 | Loesel et al. | |
| 2014/0104574 A1 | 4/2014 | Grenon et al. | |
| 2014/0128853 A1 | 5/2014 | Angeley et al. | |
| 2014/0276681 A1 | 9/2014 | Schuele et al. | |
| 2014/0343541 A1 | 11/2014 | Scott et al. | |
| 2015/0018674 A1 | 1/2015 | Scott et al. | |

* cited by examiner

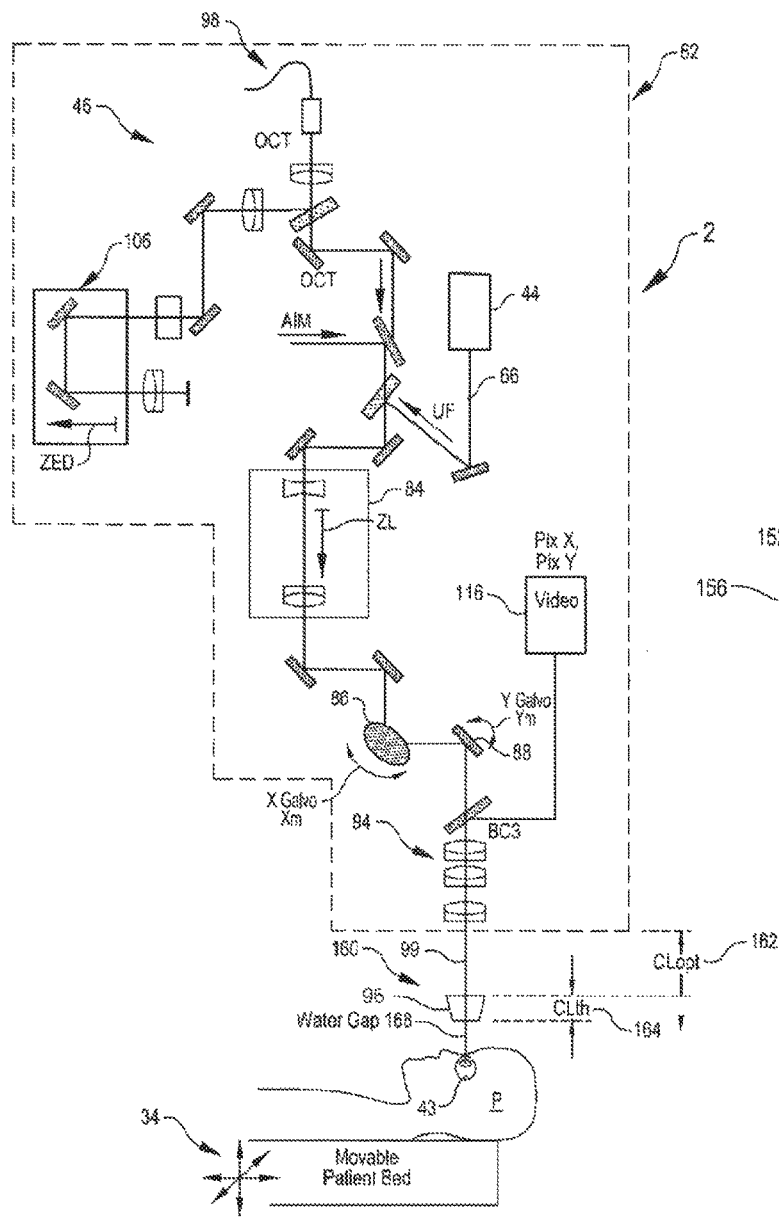
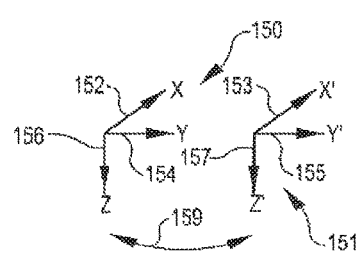
Fig. 4B
Fig. 4A

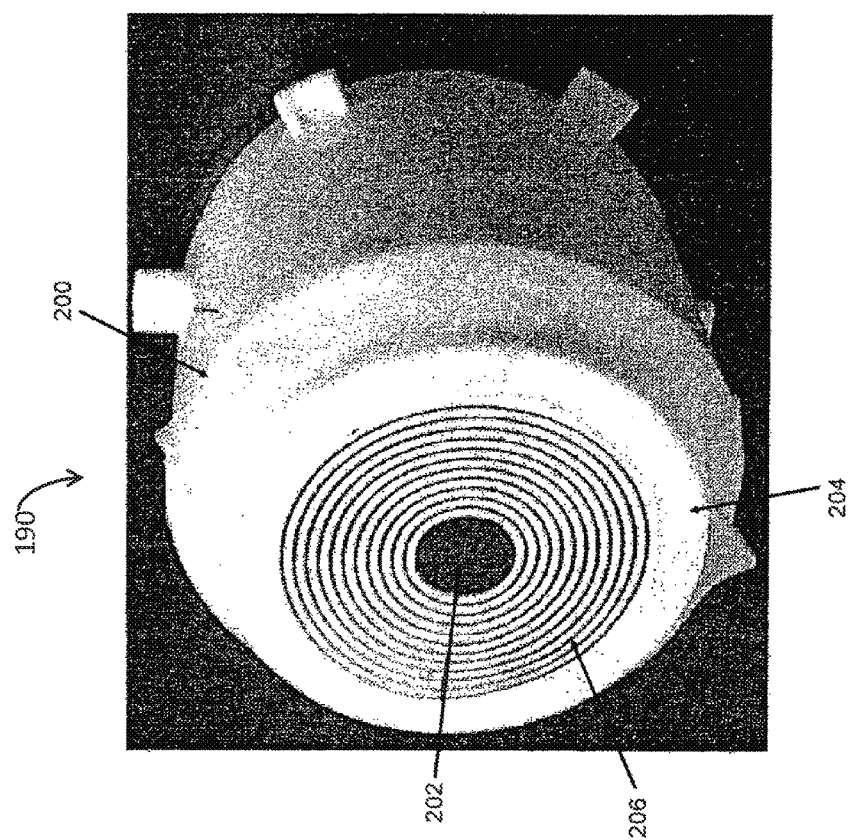

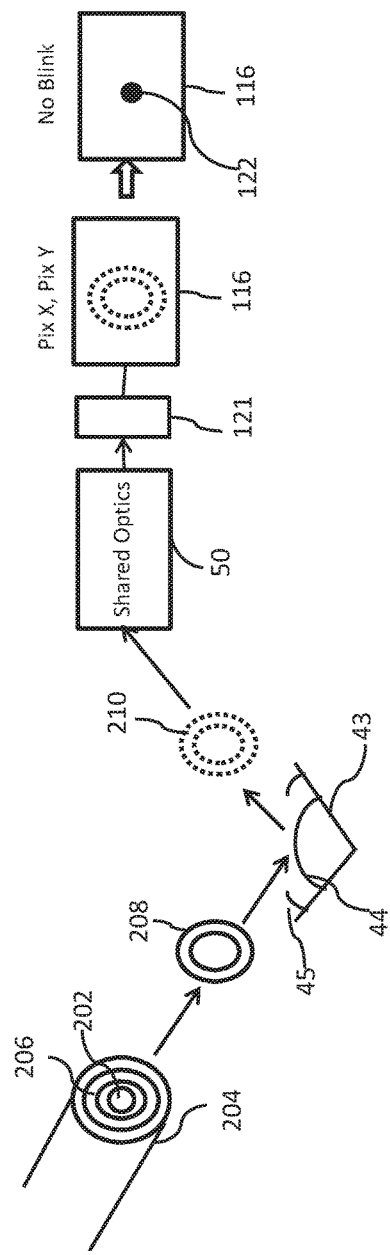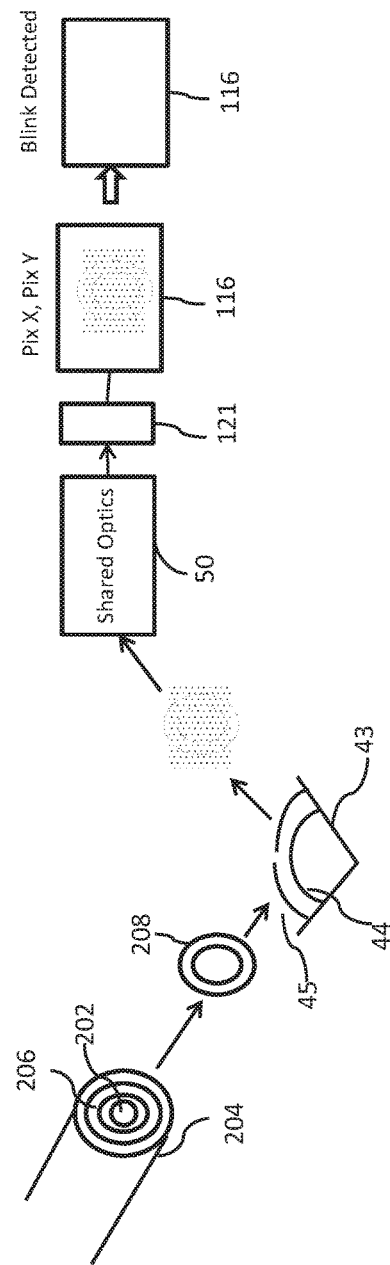
Fig. 8A
Fig. 8B

METHODS AND SYSTEMS FOR CORNEAL TOPOGRAPHY, BLINK DETECTION AND LASER EYE SURGERY

RELATED APPLICATIONS

This application is a continuation under 35 U.S.C. § 120 of U.S. patent application Ser. No. 14/866,418, filed Sep. 25, 2015, which is a non-provisional application and claims the benefit under 35 U.S.C. § 119(e) of U.S. Provisional Application Ser. No. 62/055,429, filed Sep. 25, 2014. The two applications referenced above are incorporated herein in their entireties as if fully set forth.

TECHNICAL FIELD

This disclosure relates generally to eye surgery, and more particularly, to methods and systems for corneal topography and blink detection in laser eye surgery.

BACKGROUND

Several people have vision impairments associated with refractive properties of the eye, such as myopia (near-sightedness), hyperopia (far-sightedness) and astigmatism. Myopia occurs when light focuses before the retina, and hyperopia occurs when light is refracted to a focus behind the retina. Astigmatism occurs when the corneal curvature is unequal in two or more directions. These vision impairments can be corrected with spectacles or contact lenses. Alternatively, the cornea of the eye can be reshaped surgically to provide the needed optical correction.

Eye surgery has now become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. The reason eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery.

Examples of surgically cutting eye tissues include cutting the cornea and/or the crystalline lens of the eye. The lens of the eye can be cut to remove a defect, such as a cataract. Other eye tissues, e.g. the cornea or the lens capsule may be cut to access the cataractous lens so it can be removed.

The cornea can also be cut and reshaped to correct a refractive error of the eye, for example with laser assisted in situ keratomileusis ("LASIK"), photorefractive keratectomy ("PRK"), radial keratotomy ("RK"), cornealplasty, astigmatic keratotomy, corneal relaxing incision ("CRI"), Limbal Relaxing Incision ("LRI"), and refractive lenticular extractions, such as small incision lenticular extractions, and flapless refractive lenticular extractions. With astigmatic keratotomy, corneal relaxing incisions, and limbal relaxing incisions, the corneal cuts are made in a well-defined manner and depth to allow the cornea to change shape and become more spherical.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include Abbott Medical Optics' iFS Advanced Femtosecond Laser, Abbott Medical Optics' IntraLase FS Laser, and OptiMedica's Catalys Precision Laser System.

In the commonly-known LASIK procedure, an ultra-short pulsed laser is used to cut a corneal flap to expose the corneal stroma for photoablation with ultraviolet beams from an excimer laser. Photoablation of the corneal stroma with the excimer laser reshapes the cornea and corrects the refractive condition such as myopia, hyperopia, astigmatism, and the like.

Cataract extraction is also a frequently performed surgical procedure with an estimated 15 million cataract surgeries performed per year worldwide. Opacification of the natural crystalline lens of the lens leads to cataract formation. The cataract scatters light passing through the lens, thereby perceptibly degrading vision. A cataract can vary in degree from slight to complete opacity. Early in the development of an age-related cataract, the power of the lens may increase, causing near-sightedness (myopia). Gradual yellowing and opacification of the lens may reduce the perception of blue colors as those shorter wavelengths are more strongly absorbed and scattered within the cataractous crystalline lens. Often, cataract formation progresses slowly, resulting in progressive vision loss.

Typically, cataract treatment involves replacing the opaque crystalline lens with an artificial intraocular lens (IOL). Cataract surgery can be performed using a technique called phacoemulsification, in which an ultrasonic tip with associated irrigation and aspiration ports is used to sculpt the relatively hard nucleus of the lens to facilitate its removal through an opening made in the anterior lens capsule. The outer membrane of the lens, referred to as the lens capsule, contains the nucleus of the lens, which is often the site of the highest grade of the cataract.

Performing an anterior capsulotomy or capsulorhexis in which a small round hole is formed in the anterior side of the lens capsule provides access to the lens nucleus. When a laser is used to cut the lens capsule, the procedure is called capsulotomy, whereas when forceps and other manual surgical tools are used to tear the lens capsule, the procedure is called a manual continuous curvilinear capsulorhexis (CCC). After the capsulotomy, the laser may be used to segment the cataractous lens to ease its removal from the eye. After removal of the lens nucleus, a synthetic foldable intraocular lens (IOL) can be inserted into the remaining lens capsule of the eye.

Conventional ultra-short pulse laser systems have been used to cut eye tissue, and to treat many patients with cataracts. Sometimes, however, these systems may provide less than ideal results for treatment of at least some patients' eyes. This may occur because the eye comprises complex optical structures, making the success of laser eye surgery dependent on the accurate and precise measurement of both the position of the eye in connection with laser eye surgery system, as well as the measurement and/or imaging of the eye structures themselves. For example, in some instances, misalignment of the eye with the surgical treatment apparatus may result in less than ideal placement of incisions.

Other factors that may limit the usefulness of data provided to a surgical laser system from eye measurement devices, such as tomography and topography systems. For example, there can be at least some distortion of at least some of the images taken among different devices, and this distortion can make the placement of laser incisions less than ideal in at least some instances. Also, the use of different systems for measurement and treatment can introduce alignment errors, may take more time than would be ideal, and may increase the overall cost of surgery so that fewer patients receive beneficial treatments.

Another factor that may affect the accuracy of positioning and eye structure measurement is the occurrence of blinking. Blinking is the semi-autonomic rapid closing and opening of the eyelid. A patient may reflexively blink to protect the eye from perceived potential damage, or may do spontaneously, generally at rate of 10 to 15 times a minute. Each blink lasts for 100-400 milliseconds, during which it obstructs all pattern vision and attenuates light levels 100-folds. In addition, the reflection, refraction, and/or scattering of light from the eye lid is vastly different from the reflection, refraction, and/or scattering of light off surfaces of the eye, such as the cornea. As a result, data on eye measurement and eye position based on the reflective, refractive or other properties of the eye may be less than ideal if that data was obtained during a blink.

Traditionally, the laser surgical device operator ensures that the patient is not blinking. But, the operator may miss one or more blinks while performing other tasks during eye surgery. Hence, there is a need for a blink detection system and methods that account for a patient's blinking during eye positioning and measurement.

BRIEF SUMMARY

Hence, to obviate one or more problems due to limitations and disadvantages of the related art, one object of this disclose provides embodiments for improved imaging and positioning of a patient's eye by detecting blinking during eye positioning and measurement.

A method of blink detection in a laser eye surgical system comprises providing a topography measurement structure having at least one geometric marker, and placing the topography measurement structure into a position proximal to an eye of a patient such that light traveling from the at least one geometric marker is capable of reflecting off a refractive structure of the eye of the patient. The refractive structure is the preferably the cornea and more preferably the tear film of the cornea.

The method includes detecting the light reflected from the eye of the patient for a predetermined time period while the topography measurement structure is at the proximal position, and converting the light reflected from the surface of the eye in the predetermined time period into image data. The method includes analyzing the image data to determine whether light from the geometric marker is detected in the reflected light, wherein if the geometric marker is determined not to be present, the patient is determined to have blinked during the predetermined time. If the geometric marker is determined to be present in the detected light, the patient is determined not to have blinked during the predetermined time.

The geometric marker is preferably one or more regular curves, such as one or more circles, lines, or ellipses. Preferably, the at least one geometric marker comprises a circle. Alternatively, there may be a plurality of geometric markers, and the geometric markers comprise at least two concentric circles.

In many embodiments, the step of analyzing the image data comprises performing at least one of a Hough transform of the image data, fitting the image data and measuring a goodness of fit, and image correlation with geometric marker template. In a preferred embodiment, the geometric marker is one or more circles, and data is analyzed with the Hough Transform to identify whether the one or more circles is present in the image data.

In many embodiments, the detecting step further comprises periodically re-detecting the light reflected from the surface of the eye, converting the reflected light to image data, and analyzing the image data at each occurrence of the periodic detection. In a preferred embodiment, the periodic detection corresponds to a rate of 30 Hz.

In many embodiments, to provide improved imaging and ranging, methods and systems of blink detection are used concurrently with another imaging or positioning measurement system. A method of improved imaging and ranging in a laser eye surgical system comprises providing a topography measurement structure having at least one geometric marker at a position proximal to an eye of a patient such that light traveling from the at least one geometric marker is capable of reflecting off a refractive surface of the eye of the patient. The refractive structure is preferably the cornea and more preferably, the tear film of the cornea.

The method includes generating structural or position data regarding a patient's eye, and during at least a portion of the generating step, and while the topography measurement structure is at the proximal position, periodically detecting the light reflected from the refractive structure of the patient's eye for a predetermined period of time. The method also includes converting the light reflected from the surface of the eye for at least one predetermined time period into image data, and analyzing the image data to determine whether light corresponding to the geometric marker was present in the reflected light, wherein if the geometric marker is determined not to be present, the patient is identified as having blinked in the predetermined time during the generating step. If the geometric marker is determined to be present in the detected light, the patient is determined not to have blinked in the predetermined time during the generating step.

In some embodiments, the method includes re-generating the structural or position data if it is determined that a blink occurred during the predetermined time period.

In some embodiments, the method includes identifying that the structural or position data corresponding to the time periods during which the patient has been determined to have blinked are not accurate. In some embodiment, the method includes removing structural or position data corresponding to the time periods during which the patient has been determined to have blinked.

The geometric marker is preferably one or more regular curves, such as circles, lines, or ellipses. Preferably, the at least one geometric marker comprises a circle. Alternatively, there may be a plurality of geometric markers, and the geometric markers comprise at least two concentric circles.

In many embodiments, the step of analyzing the image data comprises performing at least one of a Hough transform of the image data, fitting the image data and measuring a goodness of fit, and image correlation with geometric marker template. In a preferred embodiment, the geometric marker is one or more circles and data is analyzed with the Hough Transform to identify whether the one or more circles is present in the image data.

In many embodiments, an apparatus for detecting the blink of an eye in a patient comprises a topography measurement system having at least one geometric marker, the topography measurement system for measuring a topography of the cornea of the eye; an image capture device configured to capture an image of the light reflected from a refractive structure of the eye of the patient for a predetermined period of time; and a processor comprising a tangible medium configured to analyze the captured image to determine whether light corresponding to the geometric marker is present in the captured image, wherein if light corresponding to the geometric marker is not present in the captured image, the processor reports that the eye blinked during the predetermined time period.

In many embodiments, the blink detection methods are used concurrently with the generation of a surface profile of the cornea to determine whether the patient has blinked during the measurement of the surface. The surface profile of the cornea is measured when the eye is placed in an undistorted shape, for example, without being in contact with an external structure such as a patient interface, such that distortion of the cornea and measurement distortion is substantially inhibited. When the eye has been placed in an undistorted configuration, such as when the patient is supported with a patient support of the laser surgery system and views the fixation light, the cornea of the eye can be exposed to air with a tear film, or other liquid over the cornea. The surface profile of the substantially undistorted cornea can be measured in one or more of many ways, and may comprise one or more of an anterior corneal surface topography profile, a posterior a corneal surface topography profile, or a corneal thickness profile. In many embodiments, the surface profile comprises a representation of a three-dimensional profile, and may comprise an extraction of one or more parameters from one or more images, such as an extraction of keratometry values from a corneal topography system or a tomography system integrated with the surgical laser. The one or more parameters can be used to determine a tissue treatment pattern on the eye, such as the angular location, depth, arc length, and anterior to posterior dimensions of relaxing incisions. Alternatively, or in combination, a first image of the eye can be generated for aligning the eye, such as a pupil image of the eye when the eye rests naturally and the surface profile is measured.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE FIGURES

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 4A shows correspondence among movable and sensor components of the laser delivery system according to many embodiments;

FIG. 4B shows mapping of coordinate references from an eye space coordinate reference system to a machine coordinate reference system according to many embodiments;

FIG. 5A shows a topography measurement structure configured to couple to a patient interface to measure the eye prior to the eye contacting the patient interface according to embodiments;

FIGS. 8A and 8B illustrate the operation of a blink detection and corneal topography system according to many embodiments of the invention. FIG. 8A illustrates the operation of the corneal topography and blink detection system when the eye is open. FIG. 8B illustrates the operation of the corneal topography and blink detection system when the eye is closed.

DETAILED DESCRIPTION OF THE INVENTION

Figure 1:
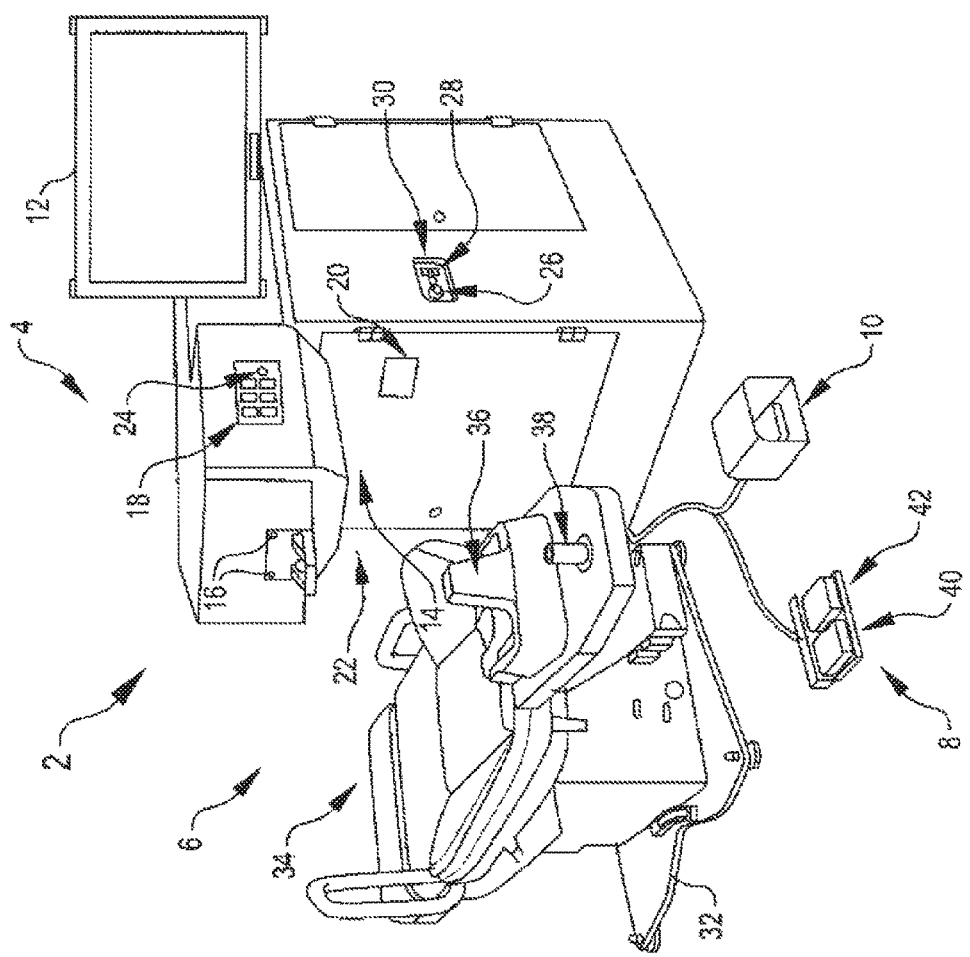
FIG. 1 shows a perspective view showing a laser eye surgery system according to many embodiments.

Methods and systems related to laser eye surgery are disclosed. In many embodiments, a laser is used to form precise incisions in the cornea, in the lens capsule, and/or in the crystalline lens nucleus. Although specific reference is made to tissue incisions for laser eye surgery, the embodiments in this disclosure can be used in one or more of many ways with many surgical procedures such as orthopedic surgery and robotic surgery, as well as with many surgical devices, including microkeratomes.

The embodiments described here are particularly well-suited for treating tissue, such as surgically treating tissue. In many embodiments, the tissue comprises an optically transmissive tissue, such as tissue of an eye. The embodiments described here can be combined in many ways with one or more of many known refractive and cataract surgical procedures, including for example, one or more procedures for laser cataract surgery, corneal incisions, LASIK, all laser LASIK, femto LASIK, corneaplasty, astigmatic keratotomy, corneal relaxing incisions, limbal relaxing incisions, PRK, RK, refractive lenticular extractions, and small incision lenticule extractions.

Methods and systems of blink detection are disclosed. These method and systems may be advantageously used in connection with other measurements, such as the determination of the position or measurement of eye structures, to determine whether a blink has occurred during the measurement.

The embodiments disclosed here are also well-suited for combination with corneal measurement systems. The corneal measurement system may comprise a component of the laser surgery system, which allows the cornea to be measured with the corneal measurement system when the patient is supported with a patient support such as a surgical bed coupled to the laser surgery system. Alternatively, the corneal measurement system may comprise a corneal measurement system separated from the laser system, such as that located in another room of a physician's office.

The embodiments disclosed here are well-suited for combination with laser surgery systems, such OptiMedica's Catalys Precision Laser System, AMO's iFS Laser System, and similar systems. Such systems can be modified according to the teachings disclosed so as to more accurately measure and treat the eye.

As used here, the terms anterior and posterior refer to known orientations with respect to the patient. Depending on the orientation of the patient during surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described here, and the terms anterior, posterior, proximal, distal, upper, and lower are used merely by way of example.

As used here, the terms first and second are used to describe structures and methods without limitation as to the order of the structures and the methods, which can be in any order, as will be apparent to a person of ordinary skill in the art based on the teachings provided here.

As used here, the term anterior and posterior nodal points of the eye may have the property that a ray aimed at one node will be refracted by the eye such that it appears to have come from the other node, and with the same angle with respect to the optical axis.

FIG. 1 shows a laser eye surgery system 2, according to many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen display control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to enable export of treatment reports to a data storage device. The treatments reports stored on the data storage device can then be accessed at a later time for any suitable purpose such as, for example, printing from an external computer in the case where the user without access to network based printing.

Figure 2:
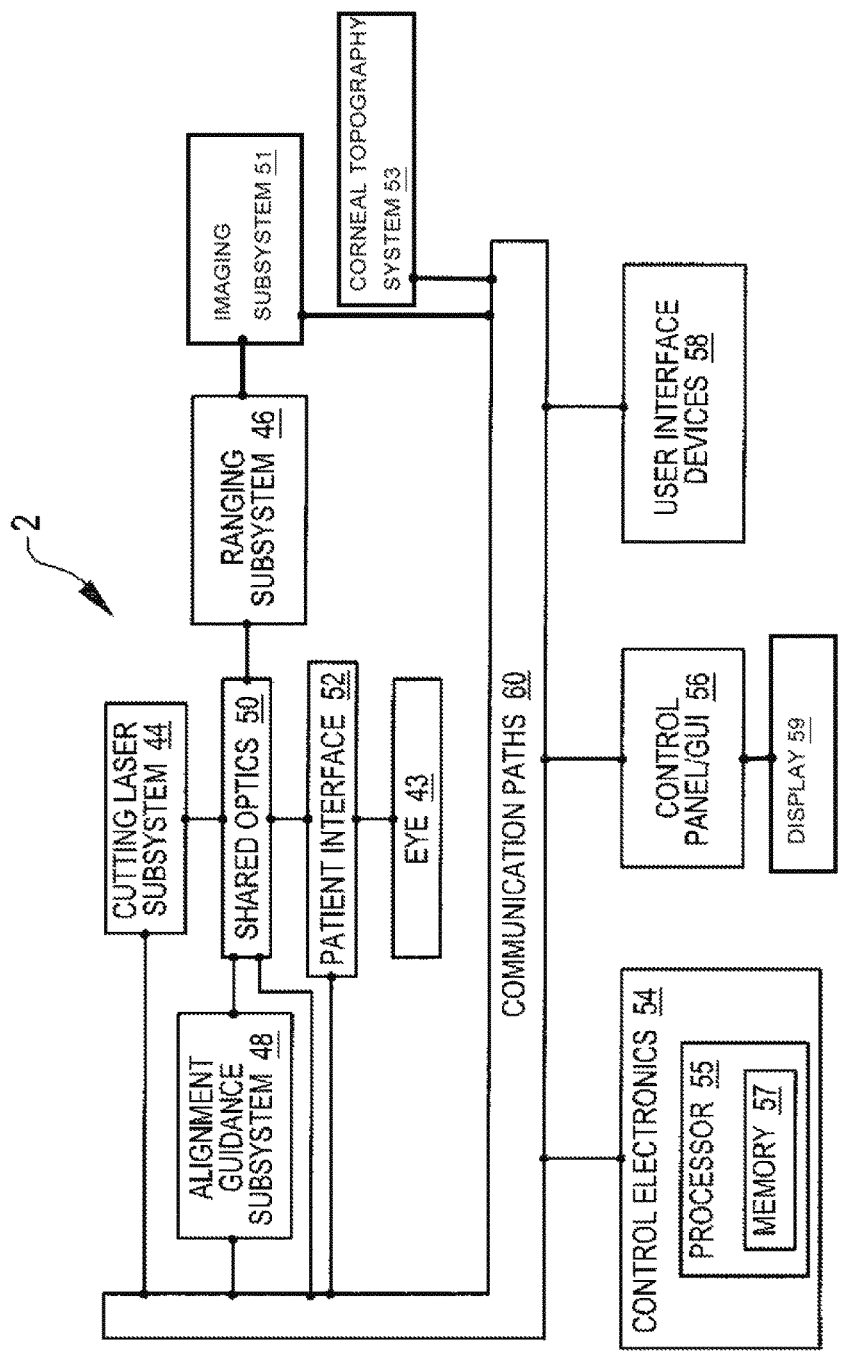
FIG. 2 shows a simplified block diagram showing a top level view of the configuration of a laser eye surgery system according to many embodiments.

FIG. 2 shows a simplified block diagram of the system 2 coupled with a patient eye 43. The patient eye 43 comprises a cornea 43C, a lens 43L and an iris 431. The iris 431 defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

The laser eye surgery system 2A comprises an imaging subsystem 51 which may be used to visualize and image the eye 43, and the control panel/GUI 56 comprises a display 59. The laser eye surgery system 2 may be configured to couple to a corneal diagnostic system 53. For the laser eye surgery system 2, the OCT system of the ranging subsystem 46 may be used to position the patient eye and/or to measure the shape of the cornea as discussed herein. For the laser eye surgery system 2, corneal topography system 53 may be used to measure the shape of the cornea. The corneal topography system 53 may apply any number of modalities to measure the shape of the eye including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, or a low coherence reflectometry of the eye. The shape of the cornea can be measured before, during, or after the patient interface 52 is docked with the eye of the patient. Images captured by the ranging subsystem 46 of the laser eye surgery system 2 or the imaging subsystem 546 of the laser eye surgery system 2 and the corneal topography system 53 may be displayed with a display of the control panel/GUI 56 of the laser eye surgery system 2 or the display 59 of the laser eye surgery system 2, respectively. The control panel/GUI 56 may also be used to modify, distort, or transform any of the displayed images.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector (not shown) to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
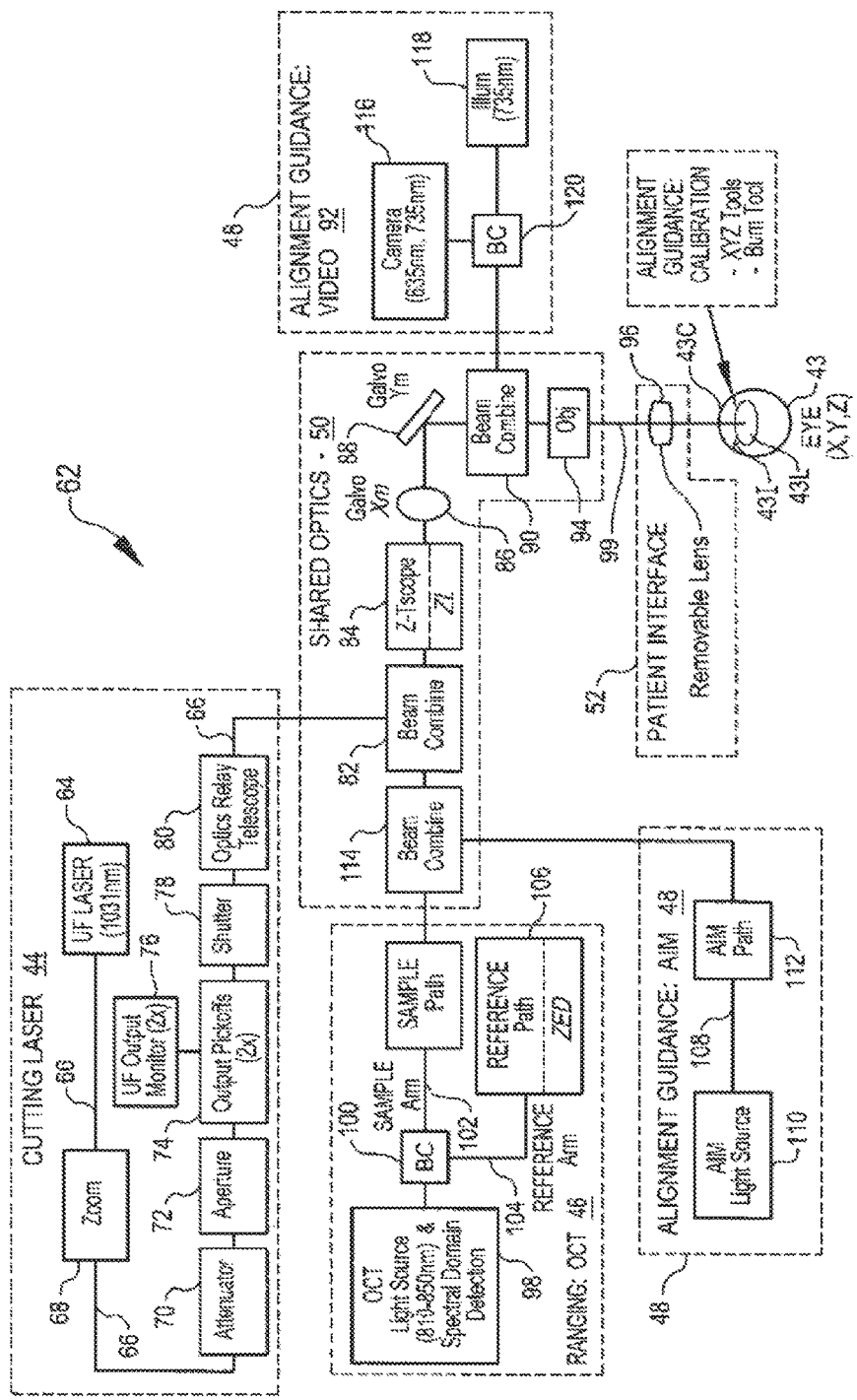
FIG. 3A shows a simplified block diagram illustrating the configuration of an optical assembly of a laser eye surgery system according to many embodiments.

FIG. 3A is a simplified block diagram illustrating an assembly 62, according to many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically, to achieve optimal performance, the transmission through this aperture is set in the range between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a Keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also, the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally, the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3A, the ranging subsystem 46 includes an OCT imaging device. Additionally or alternatively, imaging modalities other than OCT imaging can be used. An OCT scan of the eye can be used to measure the spatial disposition (e.g., three-dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3A includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber, and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc., are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively, the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
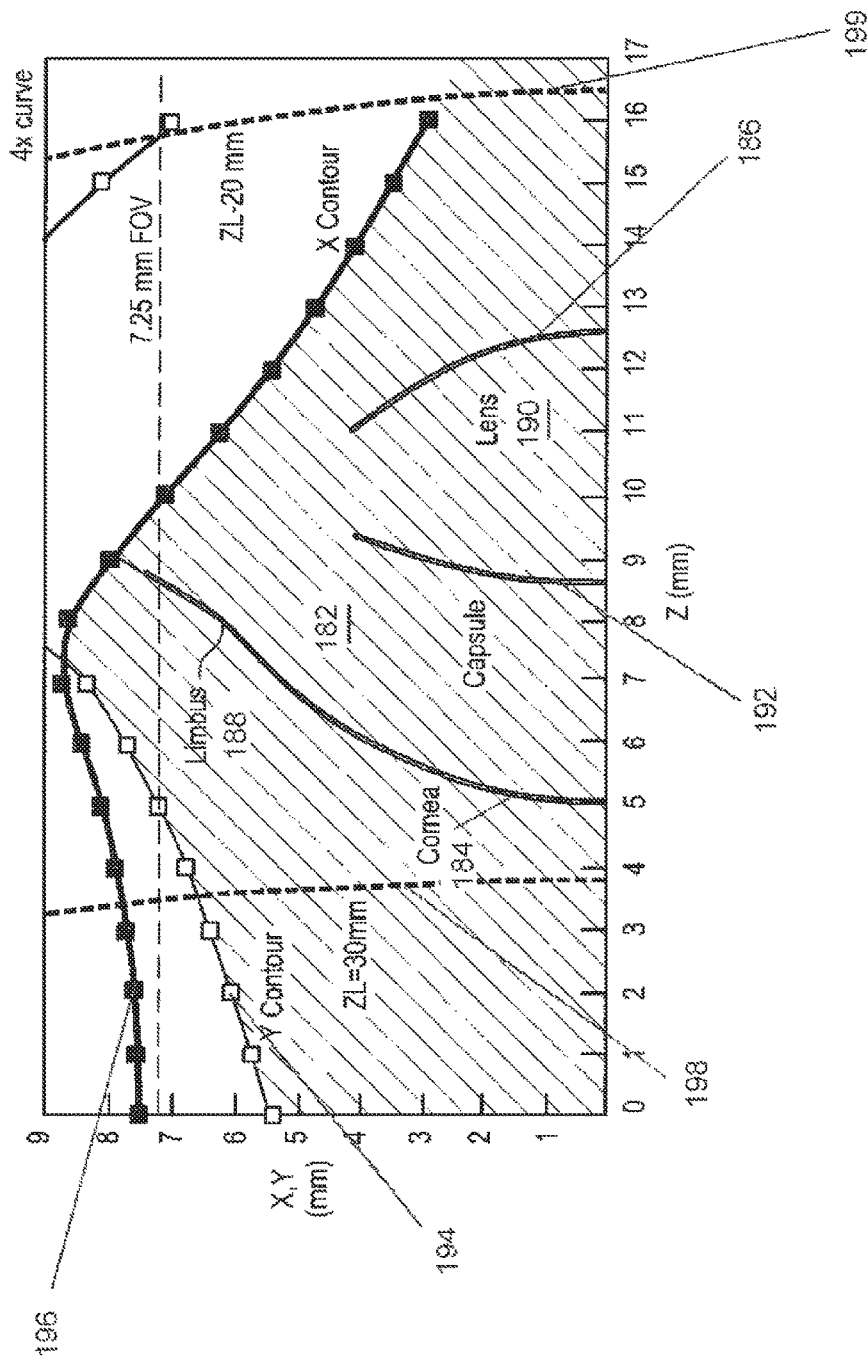
FIG. 3B shows a mapped treatment region of the eye comprising the cornea, the posterior capsule, and the limbus according to many embodiments.

FIG. 3B shows a mapped treatment region 182 (hatched area) of the eye comprising the cornea 184, the posterior capsule 186, and the limbus 188. The treatment region 182 can be mapped with computer modeling, for example ray tracing and phased based optical modeling to incorporate factors such as laser beam quality, pulse width, system transmission, numerical aperture, polarization, aberration correction, and alignment. The treatment volume 182 is shown extending along the Z-axis from the posterior surface of the optically transmissive structure of the patient interface a distance of over 15 mm, such that the treatment volume 182 includes the cornea 184, and the lens 190 in which the treatment volume of the lens 190 includes the anterior capsule 192, the posterior capsule 186, the nucleus and the cortex. The treatment volume 182 extends laterally from the center of the cornea 184 to beyond the limbus 188. The lateral dimensions of the volume 182 are defined by a Y contour 194 anterior to the limbus 188 and by an X contour 196 posterior to the limbus 188. The treatment volume 182 shown can be determined by a person of ordinary skill in the art based on the teachings described herein. The lateral positions of predicted optical breakdown for ZL fixed to 30 mm 198 and ZL fixed to 20 mm 199 are shown. These surfaces that extend transverse to the axis 99 along the Z-dimension correspond to locations of optical scanning of the X and Y galvos to provide optical breakdown at lateral locations away from the axis 99. The curved non-planar shape of the scan path of optical breakdown for ZL-30 mm 198 and ZL-20 mm 199 can be corrected with the mapping and LUTs as described herein. The curved shape of the focus can be referred to as a warping of the optical breakdown depth and the LUTs can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region 182 is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and LUTs as described here can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume 182 may optionally be adjusted with mapping based on measurements of a constructed system as described herein.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 96 capable of moving an angular amount Xm, and the Y galvo mirror 88 capable of moving an angular amount Ym. The movable components of the OCT system may comprise the movable OCT reference arm configured to move the reference path 106 a distance ZED. The sensor components of the laser system may comprise the video camera having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 168 is separated from the cornea with gap 168 extending between the lens and the vertex of the cornea, such that the posterior surface of the contact lens 168 contacts a solution comprising saline or a viscoelastic solution, for example.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example. In many embodiments the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the z-telescope lens capable of moving distance ZL. The dimension 153 may correspond to movement of the X galvo mirror 86 capable of moving an angular amount Xm, and the dimension 153 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the z-telescope lens capable of moving the distance ZL, for example. In many embodiments, the locations of the components of the laser system 2 are combined when in order to map the plurality of machine coordinate reference systems to the coordinate reference system 150 of eye 43.

In many embodiments, the eye coordinate reference system is mapped from an optical path length coordinate system to physical coordinates of the eye based on the index of refraction of the tissues of the eye. An example is the OCT ranging system where measurements are based on optical thicknesses. The physical distance can be obtained by dividing the optical path length by the index of refraction of the material through which the light beam passes. Preferable the group refractive index is used and takes into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X- and Y-directions, and departure from the telecentric condition occurs due to the axial location of the galvo mirrors, a distortion of the optical path length is realized. This is commonly known as fan error, and can be corrected for either through modeling or measurement.

As one or more optical components and light sources as described here may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both, the phase and group index, can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 nm. The group refractive index of 1.339 differs on the order of 1% for the OCT beam wavelength and spectral bandwidth. A person of ordinary skill in the art can determine the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

FIGS. 5A-5F show a topography measurement structure configured to couple to a patient interface 52 as described here to measure the eye prior to the eye contacting the patient interface. The topography measurement structure may comprise one or more of a ring or other structure for a keratometry reading of the eye, a Placido disc topography of the eye, a reflection of a plurality of points from the cornea topography of the eye, a grid reflected from the cornea of the eye topography. In many embodiments, the measurement structure comprises a Placido disc structure configured to couple to a component of the patient interface, for example. The topography measurement structure can be illuminated, for example, so as to form a virtual image of the measurement structure when reflected from the cornea. One illumination strategy could make use of the internal existing illuminator of the system itself. Alternatively or in combination, the topography structure may comprise a ring illuminator either mounted to the patient interface or to the structure of the laser system.

One embodiment of the topography measurement structure is shown for instance in FIG. 5A. The topography measurement structure 195 generally comprises a first end 204 to be brought into a proximal position to a patient's eye and a second end 200 opposite the first end that is configured for attaching to the patient interface. The first end 204 generally comprises one or more geometric markers 206 that will be used for blink detection of the patient's eye. In a preferred embodiment, the same geometric markers 206 may also be used for measurement of the corneal topography. This is, however, not strictly required. The first end may comprise one or more geometric markers for blink detection and one or more different geometric structures for topography measurement. The first end also comprises an aperture 202 that allows light to pass through the first end 204 of the topography measurement structure 195. Another embodiment of the topography measurement structure 195 according to the present invention is shown, for instance, in FIGS. 5D, 5E and 5F.

The specific shape of the geometric marker at the first end 204 is not particularly limited. Preferably, the geometric marker includes at least one circle. In another embodiment, the geometric marker comprises two or more concentric circles. Other permissible geometric permissible geometric markers include lines and ovals.

In many embodiments, topography measurement structure including the geometric marker 206 is back illuminated with light from the laser system to illuminate the eye with the geometric marker 206. Alternatively or in combination the topography measurement structure 195 may comprise a plurality of light sources (not shown) such as light emitting diodes to illuminate the eye with the topography measurement structure 195 including the geometric marker 206.

Figure 5C:
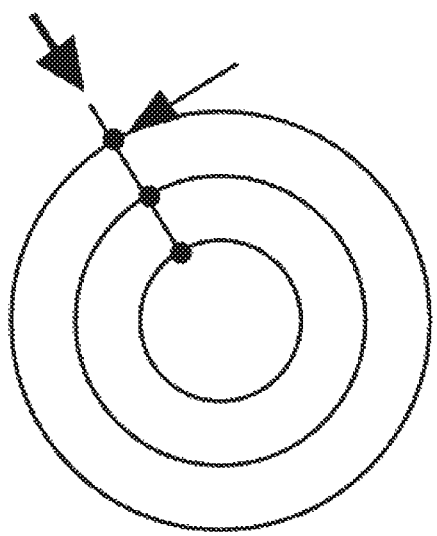
FIG. 5C shows discrete points of reflected light from the cornea based on the geometric marker of topography measurement structure.
Figure 5B:
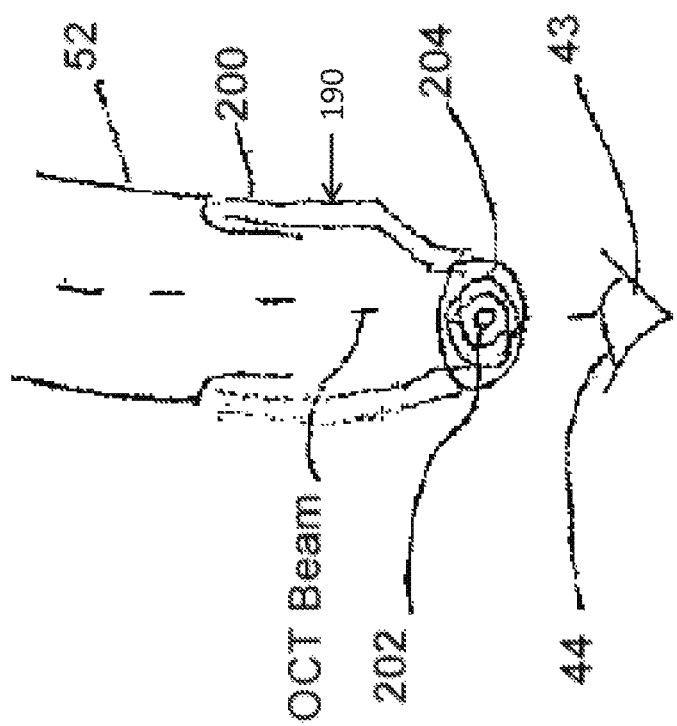
FIG. 5B shows components of the patient interface and the topography measurement structure configured to couple to the patient interface according to many embodiments.
Figure 5E:
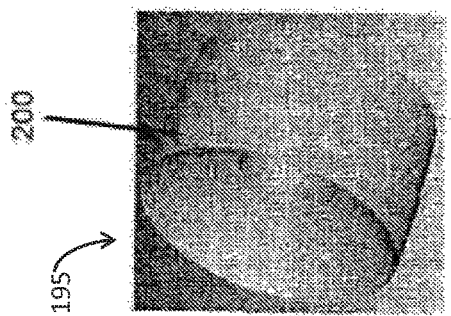
FIG. 5E shows a perspective view of the interface end of the topography measurement structure.
Figure 5F:
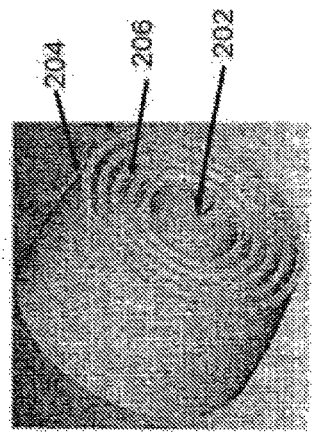
FIG. 5F shows a perspective view of the working end of the topography measurement structure.

FIG. 5B shows the topography measurement structure 195 including one or more geometric marker removably coupled to the patient interface to position the topography measurement structure 195 in relation to the eye when the patient has been placed on the support of the laser eye surgery system as described herein. An OCT beam is shown passing through aperture 202 of the topography measurement structure 195, which permits OCT measurements to be mad simultaneously and in conjunction with the topography measurement structure 195.

The OCT measurement beam can be used to position the eye. This use of the OCT measurement beam may be particularly important to achieve absolute curvature readings of the Placido system as the diameter of the reflected Placido rings may depend not only on the curvature of the cornea but also from the distance of the ring illuminator and the cornea. OCT can help to minimize these variations. Additionally, this measurement information can also be used to actively track position the patient's chair and move the eye into the correct or desired position. Additionally, the OCT system and optionally also the camera can be used to locate the actual position of the concentric rings in relation to the system to enable high precision measurements. Alternatively or in combination, the focus of the video camera as describe here can be used to position the eye for measurement. When the topography of the patient has been measured and the axis determined, for example, the topography measurement system can be decoupled from the patient interface structure and the patient interface coupled to the eye as described herein.

The illuminator can be constructed in many different ways. Having a clear aperture in the center of the ring structure to allow the video system to be used as is may be particularly important. Other embodiments may comprise a combination of different engineered diffusers and masks which can be optimized on the diffusing angle used to the detection of the rings from the cornea. Or, if polarized light is used, a combination of quarter wave plate or depolarizer and diffuser with ring apertures can be used. For full utilization, the light illuminated on the blocked rings can make the blocked rings act as reflecting wedges so the light is fully utilized. In such cases, an angle which enables total reflection may be helpful. Utilizing a combination of a strong negative lens and the Placido disk illuminator can also increase the light intensity of the outer rings for better contrast.

In many embodiments, the topography measurement structure comprises an external illumination structure such as a ring illuminator illuminates the eye to form a ring shaped virtual image of the illumination structure, and the astigmatic axis of the eye determined based on measurements of the virtual image of the eye as described herein. The external illuminator can be configured to couple to the patient interface for measurement of the eye and removed when the eye has been docked to the patient interface. Alternatively, the external illuminator may comprise a substantially fixed structure that remains fixed to the laser system throughout a plurality of procedures.

The corneal topography data and thickness data can be combined in one or more of many ways. For example, the corneal topography data can be used to determine the shape profile of the anterior corneal surface, and the corneal thickness profile data can be fit to the anterior corneal surface profile in order to determine the profile of the posterior surface, for example. In many embodiments, the anterior corneal surface profile is measured and determined without the patient interface contacting the eye, and the corneal thickness profile is measured and determined when the patient interface contacts the eye. The corneal surface profile data measured without contacting the eye can be combined with the corneal thickness profile data measured with the patient interface contacting the eye, and the location of refractive incisions determined in response to both profiles, for example.

As illustrated in FIG. 5C, light reflected by the cornea is generally measured at discrete points, preferably along multiple radial lines to determine the existence and nature of the virtual image formed when light is reflected off the cornea.

Figure 5D:
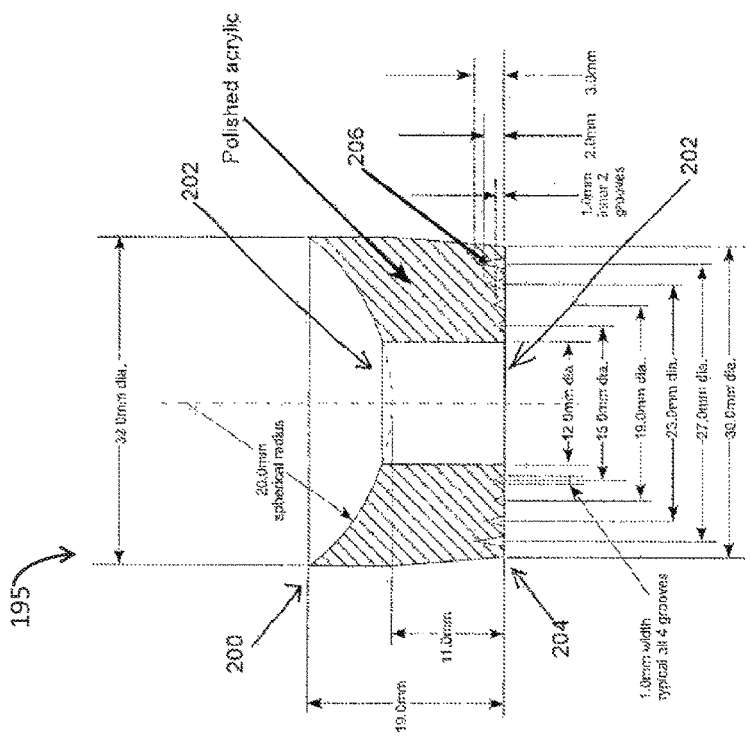
FIG. 5D shows components of the patient interface and the topography measurement structure configured to couple to the patient interface.

FIG. 5D shows components of the patient interface and the topography measurement structure configured to couple to the patient interface.

Figure 6:
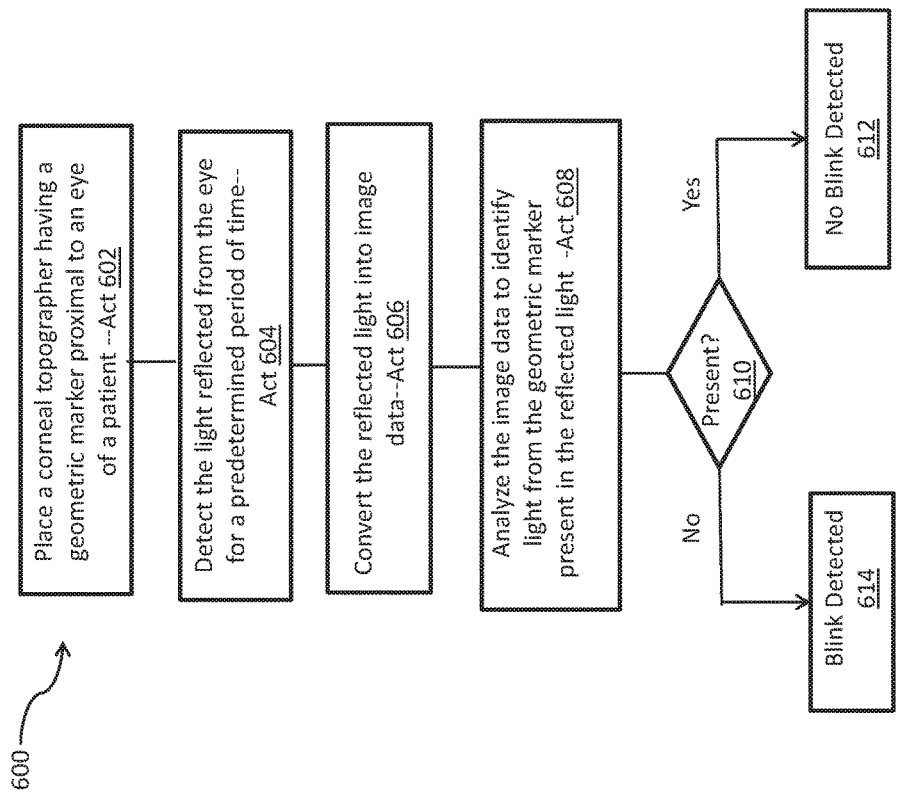
FIG. 6 shows a flow chart for performing a method of blink detection 600 in a laser eye surgical system.

FIG. 6 shows a flow chart for performing a method of blink detection 600 in a laser eye surgical system. The method includes providing a topography measurement structure having at least one geometric marker and placing the topography measurement structure into a position proximal to an eye of a patient such that light traveling from the at least one geometric marker is capable of reflecting off a refractive structure of the eye of the patient (Act 602). A detecting step includes detecting the light reflected from the eye of the patient for a predetermined time period while the topography measurement structure is at the proximal position (Act 604). The method includes converting the light reflected from the surface of the eye in the predetermined time period into image data (Act 606) and analyzing the image data to determine whether light from the geometric marker is detected in the reflected light (Acts 608 and 610). If the geometric marker is determined not to be present in the reflected light, the patient is identified as having blinked during the predetermined time (Act 612). If the geometric marker is determined to be present in the reflected light, the patient is determined to not have blinked during the predetermined time period.

The patient's eye may be positioned proximal to an eye of a patient such that light traveling from the at least one geometric marker is capable of reflecting off a refractive structure of the eye of the patient within the capture range of the measurement system of the laser eye surgery system as described herein, such as shown in FIG. 2. In many embodiments, positioning of the patient for laser surgery is typically enabled by motion of the patient bed 34 or by motion of the laser system 2. Typically, the operator has manual control of the lateral and axial position, guiding the docking mechanism or patient interface 52 into place in a step 528. In the absence of a docking mechanism, an operator means for guiding the motion so that the eye, and specifically the cornea, is placed within the operative range of the measurement system may be provided. This can be accomplished with the use of subsystems of the laser system 2 described here such as alignment guidance system 48 of laser system 2 or imaging subsystem 51. Initial patient position can be guided by a video camera, guiding the eye into lateral position by centering the video image, and into axial position by focusing the image.

In the detecting step, light reflected from the eye of the patient is directed to a detector through a predetermined optical path. The propagation of the reflected light to the detector may be achieved in many ways. In many embodiments, the reflected light is directed by shared optics 50 of the laser system of FIGS. 2 and 3A. In one embodiment, illumination light is directed through from the illumination light source 118 is transmitted through the beam combiner 120 to the beam combiner 90 and is directed towards the patient's eye 43 through the objective lens assembly 94 and through the patient interface 52, which includes a topography measurement structure having the one or more geometric markers 206. The illumination light is then scattered off of cornea of the eye 43 and patient interface and travel back through the patient interface 52, back through the objective lens assembly 94, and back to the beam combiner 90. At the beam combiner 90, the returning light is directed back to the beam combiner 120 where the returning light is redirected toward the camera 116. Alternatively, the illumination and camera paths can be switched.

The manner in which the reflected light is converted into image data is not particularly limited. For instance, the reflected light may be directed to photodetector. The type of image data, including the data type and format, that may be used in connection with the methods of the present invention is not particularly limited. The data is preferably pixel data.

Once the reflected light is converted into image data, it must be analyzed for the presence of a shape corresponding to the shape of geometric marker 206. A preferred embodiment is to use the Hough Transfer to detect geometric marker 206 within the image data. One advantage of the Hough transform technique is that it is tolerant of gaps in feature boundary descriptions and is relatively unaffected by image noise.

The Hough transform can be used to analyze the image data to identify and isolate geometric marker 206 within the image. The Hough transform is generally used for the detection of regular curves such as lines, circles, ellipses, etc., and thus, is particularly-suited when geometric markers 206 in the form of lines and circles are selected. Although a generalized Hough transform may be employed in applications where a simple analytic description of geometric marker 206 is not possible, computational complexity and speed are limiting factors in the use of a generalized Hough algorithm. Therefore, in a preferred embodiment, analysis using the Hough transform should generally be limited to regular curves, and especially lines, circles and ellipses. The use of the Hough transform to detect ellipses may be particularly suitable in the case of astigmatic eyes, in which circular forms may be reflected off a patient's eye as ellipses. But, even in the case of astigmatic or other non-standard shaped eyes, the reflected shape of a circular form is sufficiently circular that the Hough transform for circles is suitably accurate for detecting a blink of the patient's eye.

As would be understood by those of ordinary skill, the Hough transform identifies the parameter(s) of a curve which best fits a set of given edge points. The edges may be obtained from a known feature detecting operator such as the Roberts Cross, Sobel or Canny edge detector and may be noisy, i.e. it may contain multiple edge fragments corresponding to a single whole feature. The output of an edge detector defines where features are in an image. The Hough transform determines what the features are (i.e. it detects the feature(s) for which it has a parametric (or other) description) and how many of them exist in the image.

Where the geometric marker 206 is one or more circles, the Hough transform can be used to determine the presence and parameters of a circle or circles, if any, that are present in image data when a number of points that fall on the perimeter are known. A circle with radius R and center (a,b) can be described with the parametric equations $$x = a + R\cos(t)$$

$$y = b + R\sin(t),$$

when the angle t sweeps through the full 360 degree range the points (x,y) trace the perimeter of a circle.

When the image data corresponding to the reflected image from the eye contains sufficient points, some of which fall on perimeters of circles, the Hough Transform finds parameter triplets (a,b,R) to describe each circle present in the image data, thus determining the presence of light, if any, corresponding to geometric marker 206 in the image data.

Preferably, the radius of geometric marker 206 is known radius R. If the circles in an image are of known radius R, the locus of (a,b) points in the parameter space fall on a circle of radius R centered at (x,y). The true center point will be common to all parameter circles, and can be found with a Hough accumulation array. In this case, the presence or absence of the geometric marker 206 in the image data can be determined with reference Hough accumulation array, and particularly the determination of whether accumulation array has a true center. Alternatively, the search for circles with unknown radius can be conducted by using a three dimensional accumulation matrix. When the Hough Transform identifies the presence of the geometric marker in image data, the eye is determined to be open, and it is determined that the patient did not blink. When the Hough Transform does not find the presence of the geometric marker in the image data, the eye is determined to be closed, and it is determined that the patient blinked.

When the Hough Transform is used to analyze the image data, pre-processing of the image data, such as smoothing of the image data is preferably performed.

Alternative data analysis to the Hough Transform for detection of geometric marker 206 in the image data include fitting circles and measuring the goodness of fit or image correlation with a template of the same shape as geometric marker 206.

Figure 7B:
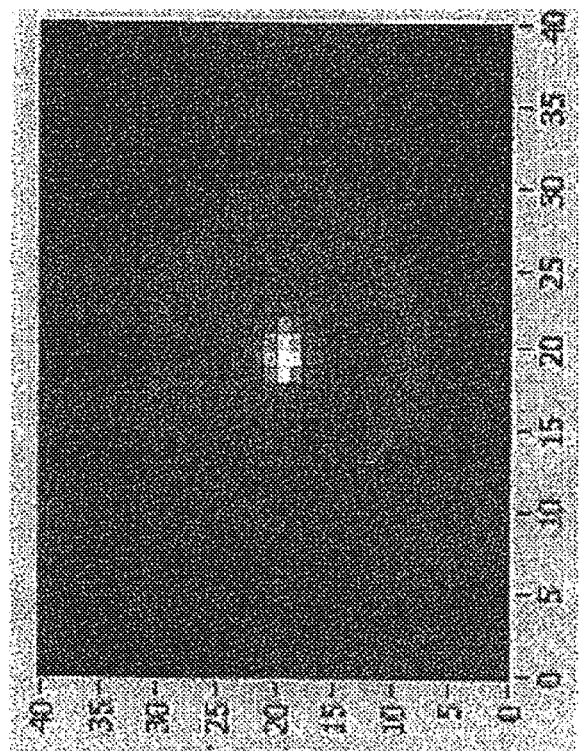
FIG. 7B shows the result of the circular Hough Transform in parameter space (a,b).
Figure 7A:
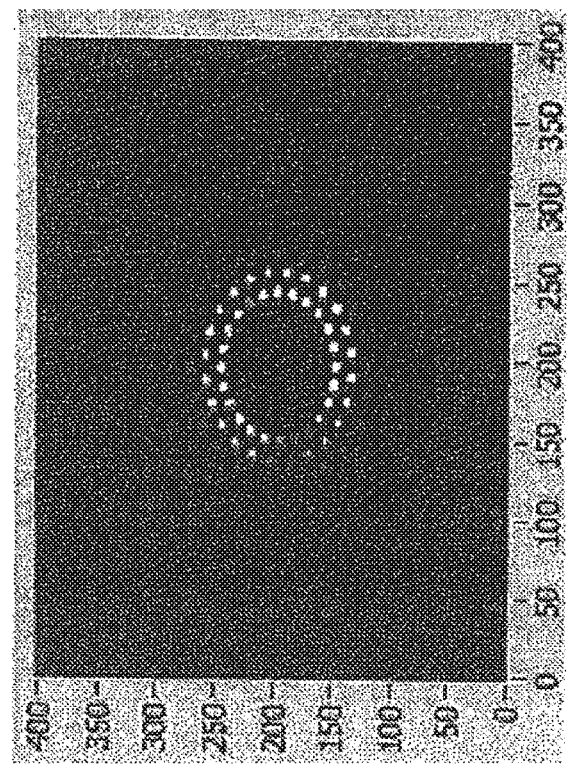
FIG. 7A shows displayed image data of a geometric marker in the case where the geometric marker is two concentric circles.

FIG. 7A shows image data of a geometric marker 206 in the case where the geometric marker 206 is two concentric circles. FIG. 7B shows the results of the circular Hough transform in parameter space (a,b). FIG. 7B shows a region of high intensity, or a "hotspot" corresponding to a true center in the accumulation array, thus indicating the presence of a circular geometric marker in the image data. Based on presence of the "hotspot," i.e. a true center in the accumulation array, it is determined that the eye did not blink at the time the reflected light from the cornea was detected.

In the blink detection method and system of the present invention, the time period over which the image data is collected is not particularly limited. Collection of the image data may begin immediately when the topography measurement structure is placed proximal to the eye of the patient or at any subsequent point at the discretion of the operator. For blink detection, the reflected light is detected during a discrete predetermined time period, and the detected reflected light for that time period is converted to image data. The reflected light is preferably periodically re-measured, and the reflected light corresponding to each time period is preferably converted to image data and preferably stored in memory. In this manner, the occurrence of patient blinking over time may be collected in stored in memory. The collected data may be used at later time to identify which The predetermined time period during which reflected light is detected should generally be long enough to allow for sufficient light to be measured by the detector system but should be short enough to resolve a blink of an eye. The blink of an eye is estimated to take up to 100 to 400 milliseconds. The predetermined time period for measurement is preferably less than 400 milliseconds, more preferably less than 100 milliseconds. Preferably, the reflected light is preferably periodically re-measured at a rate of at least 2 Hz, more preferably at least 10 Hz, more preferably at least 20 Hz, and even more preferably 30 Hz or more.

FIGS. 8A and 8B illustrate a blink detection and corneal topography method and system according to many embodiments of the invention. FIG. 8A illustrates the operation of the corneal topography and blink detection system when the eye is open. FIG. 8B illustrates the operation of the corneal topography and blink detection system when the eye is closed.

In FIG. 8A, the topography measurement structure including the geometric marker 206 is arranged in a position proximal to the eye 43 of the patient such that light originating from the at least one geometric marker 206 is capable of reflecting off the cornea 44 of the patient's eye when lid 45 is open. The geometric marker 206 is illuminated and a light pattern 208 corresponding to the geometric marker 206 is directed from the first end of the topography measurement structure to the eye 43 of the patient. The light reflected from the patient's eye forms a virtual image 210 that is directed by the shared optics 50 to a detector 121, is converted to image data in the form of pixel data, Pix X and Pix Y, and is displayed via camera 116. The image data is then analyzed to determine whether light corresponding to the virtual image 210 having the shape of geometric marker 206 was detected by the detector 121. Specifically, in FIG. 8A, the geometric marker 206 is in the shape of concentric circles, and as such, the image data is analyzed (by, for example, the Hough transform) to determine whether a circle is present in the image data. If the image data is determined to include the shape of the geometric marker, than it is determined that the patient did not blink (i.e., the patient's eye was open). In a preferred embodiment, a visual indication 122, corresponding for example to the location of a true center in parameter space, is provided on camera 116 indicating that the patient did not blink.

In FIG. 8B, the patient's eye lid 45 is closed and thus covers the top surface of the cornea 44. As in FIG. 8A, the topography measurement structure, including the geometric marker 206 is arranged in a position proximal to the eye 43 of the patient such that light originating from the at least one geometric marker 206 is capable of reflecting off the cornea 44 of the patient's eye when lid 45 is open. Further, the geometric marker 206 is illuminated and a light pattern 208 corresponding to the geometric pattern 26 is directed from the first end of the topography measurement structure to the eye 43 of the patient. However, the surface of the eyelid and the eye lash (not shown) do not efficiently reflect light and the light is scattered of the lid, such that no virtual image of the geometric marker 206 is formed in the light directed by the shared optics to the detector 121. The light detected by the detector 121 is converted to image data in the form of pixel data, Pix X and Pix Y, and is displayed via camera 116. The image data is then analyzed to determine whether light corresponding to the virtual image 210 having the shape of geometric marker 206 was detected by the detector 121. Specifically, in FIG. 6A, the geometric marker 206 is in the shape of a circle, and as such, the image data is analyzed to determine whether a circle is present in the image data. If the image data is determined to not include the shape of the geometric marker, than it is determined that the patient did not blink (i.e. the patient's eye was open). Although not shown in the Figure, a visual indication may be provided indicating that the patient blinked.

As shown in FIG. 5B, aperture 202 in the first end 204 of the topography measurement structure permits other light based measurements and procedures, such as an OCT measurement beam to pass through the topography measurement structure 109. The blink detection methods and systems of FIGS. 5-8 thus may be concurrently with other techniques designed to measure the structure or position of the eye. The nature of the concurrent measurement is not particularly limited and may generally be any measurement directed to generating structural or position data of the eye of the patient, including ranging, corneal topography, tomography, and laser surgical eye procedures.

In many embodiments, the blink detection methods described here will correlate in time with other measurements, or actions taken by the surgical system. This may be accomplished for instance, by detecting reflected light from the geometric pattern 206 at predetermined time periods during the time period one or more other measurements is carried out so that blink detection and the other measurement, and their respective data, are both performed and stored the same time, T, in the measurement process. When blink detection is carried out concurrently with another structural or position measurement, blink detection may be shown in "real time," that is, as the concurrent measurement is being carried out. The image data may also be stored for later analysis or processing to determine whether a blink occurred during at least a portion of the time the concurrent measurement was taken. If a blink is detected during the concurrent measurement, the concurrent measurement may be re-done. Alternatively, data corresponding from the concurrent measurement at times a blink is determined to have occurred may be eliminated from further use in data processing or analysis during any post-processing.

A method of improved imaging and ranging in a laser eye surgical system, comprises providing a topography measurement structure having at least one geometric marker into a position proximal to an eye of a patient such that light traveling from the at least one geometric marker is capable of reflecting off a refractive surface of the eye of the patient. The refractive surface is preferably the cornea, and may be the tear film of the cornea. The method includes generating structural or position data regarding an eye of a patient, and during at least a portion of the generating step and while the topography measurement structure is at the proximal position, periodically detecting the light reflected from the refractive structure of the eye of the patient for a predetermined period of time. The method further includes converting the light reflected from the surface of the eye for at least one predetermined time period into image data; and analyzing the image data to determine whether the geometric marker was present in the reflected light, wherein if the geometric marker is determined not to be present, the patient is determined to have blinked during the predetermined time. if the geometric marker is determined to be present, the patient is determined not to have blinked during the predetermined time The method further comprising re-generating the structural or position information regarding the eye of the patient if the patient was determined to have blinked during the eye measure. Alternatively, the method includes identifying that the structural or position data corresponding to the time periods during which the patient has been determined to have blinked are not accurate, and preferably removing structural or position data corresponding to the time periods during which the patient has been determined to have blinked.

In many embodiments, the least one geometric marker comprises a circle. Alternatively, there is a plurality of geometric markers, and the plurality of geometric markers comprises at least two concentric circles.

The step of analyzing the image data comprises performing at least one of a Hough transform of the image data, fitting the image data and measuring a goodness of fit, and image correlation with geometric marker template. In many embodiments, the Hough Transform is selected.

Figure 9:
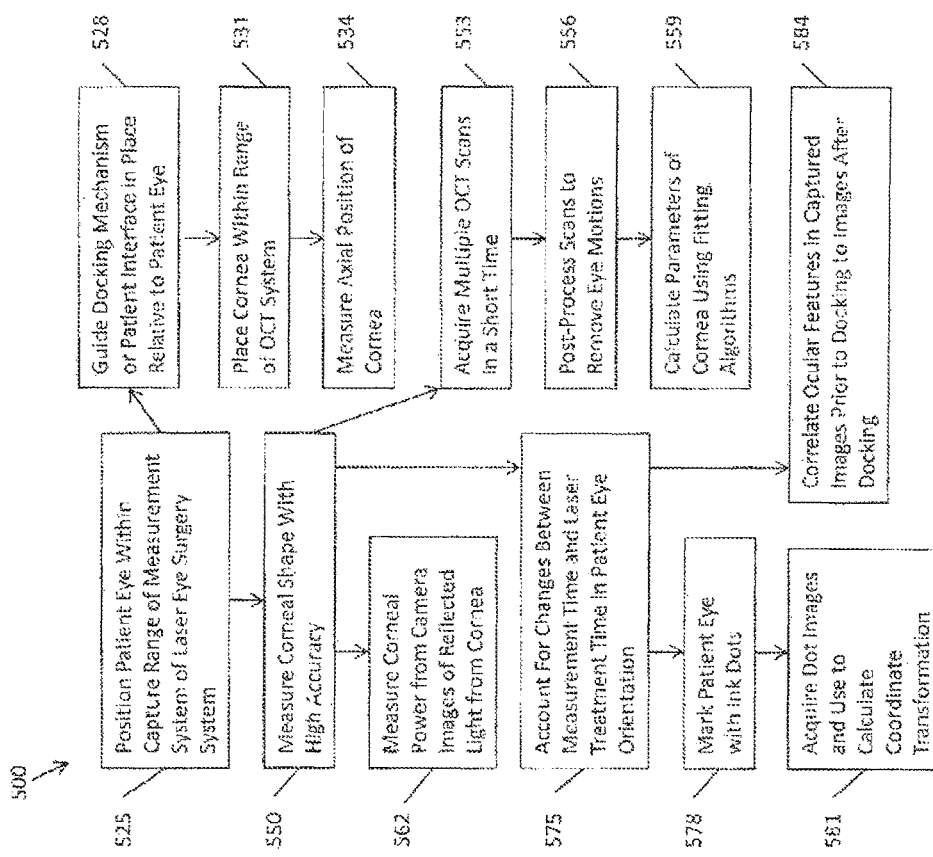
FIG. 9 shows a flow chart of a method for providing accurate and distortion-free corneal topography measurement and subsequent integration with the laser treatment, according to embodiments.

FIG. 9 shows a flow chart of a method 500 for providing accurate and distortion-free corneal topography measurement and subsequent integration with the laser treatment, according to embodiments. The blinking detection method and system described here may be advantageously used concurrently with many aspects of the corneal topography and laser treatments. The method 500 comprises the following main steps. In a step 525, the patient's eye is positioned within the capture range of the measurement system of the laser eye surgery system 2 or 2A described herein. In a step 550, the measurement system is used to measure corneal shape with high accuracy. Such a measurement system may comprise the ranging subsystem 46 described above. In a step 575, any changes in the patient eye orientation that may occur between the measurement time and the laser treatment time is accounted for in post-processing.

Positioning step 525: In the step 525, the patient's eye is positioned within the capture range of the measurement system of the laser eye surgery system as described herein, such as shown in FIGS. 2 and 3A, for example. Positioning of the patient for laser surgery is typically enabled by motion of the patient bed 34 or by motion of the laser system 2. Typically, the operator has manual control of the lateral and axial position, guiding the docking mechanism or patient interface 52 into place in a step 528. In the absence of a docking mechanism, an operator means for guiding the motion so that the eye, and specifically the cornea, is placed within the operative range of the measurement system may be provided. This can be accomplished with the use of subsystems of the laser system 2 described here, such as alignment guidance system 48 of laser system 2, or imaging subsystem 51. Initial patient position can be guided by a video camera, guiding the eye into lateral position by centering the video image, and into axial position by focusing the image. At this point, the cornea is placed within the capture range of the OCT system of the ranging subsystem 46 or imaging subsystem 546, typically X mm to Y mm axially, in a step 531. The OCT system can be used to measure the axial position of the cornea in a step 534, and a suitable display provides the operator guidance for final, accurate positioning. Alternatively, a visual imaging system such as a camera, a camera coupled to a microscope which may share optics with the laser system 2 or 2a, a CCD, among others may be used instead of the OCT system to facilitate the positioning step 525.

The blink detection and methods described here are preferably used concurrently with the OCT measurement beam to detect the occurrence of blinks during the positioning measurement. This concurrent use of the OCT measurement and blink detection may be particularly important to achieve absolute curvature readings of the Placido system, as the diameter of the reflected Placido rings may depend not only on the curvature of the cornea, but also on the distance of the ring illuminator and the cornea. OCT and blink detection can help to minimize these variations. Additionally, this measurement information can also be used to actively track position the patient's chair and move the eye into the correct or desired position. In connection with any of these uses, the blink detection method and system may be used concurrently to identify any blinking during the OCT measurement, especially during critical OCT measurements. As a result, the measurement can be re-done. Alternatively, the measurement data corresponding to the blink can be eliminated from data processing and measurement calculations.

Since the video and OCT systems are typically configured to operate with the docking system, which often has additional optical elements and liquid medium in the optics path, the focusing algorithms of the laser system may be adjusted to account for operation without the docking mechanism optics and interface medium.

Measurement step 550: In the step 550, the measurement system is used to measure corneal shape with high accuracy. The laser system 2 or 2A comprises a subsystem for mapping the ocular surfaces that are being treated such as the ranging subsystem 46 having an OCT system described here, or the imaging subsystem 546. As described below, the imaging subsystem 546 may apply other modalities for mapping the ocular surfaces such as Placido imaging, Hartmann-shack wavefront sensing, confocal tomography, low coherence reflectometry, among others. The measurement step 550 can be performed once the eye is positioned correctly in the step 525 above. A fixation light can optionally be introduced to help the patient keep the eye pointed at a fixed angle. If the measurement data capture is sufficiently fast, for example, on the order of one second, a fixation light may not be necessary. In a step 553 of measurement 550, multiple OCT or other scans of the cornea surfaces can be acquired in a short time. Multiple scans can increase the confidence of obtaining good data. In a step 556, post-processing of the scans can remove potential eye motion and further improve the measurement accuracy. In a step 562 of measurement step 550, corneal power can be measured from camera images of reflected light from the cornea.

Once the cornea surfaces have been mapped, polynomial, or other fitting algorithms can be used to calculate commonly used parameters of the cornea in a step 559. Commonly used parameters include the optical power of the cornea, astigmatic axis angle, and astigmatism magnitude.

The blink detection and methods described here are preferably used concurrently with the measurement of the corneal shape to detect the occurrence of blinks during the measurement. This concurrent use of the corneal shape measurement and blink detection allows for the determination of whether a blink has occurred during the measurement. As a result, the measurement can be re-done. Alternatively, the measurement data corresponding to the blink can be eliminated from data processing and fitting calculations.

Coordinate system transfer step 575: In the step 575, any changes in the patient eye orientation that may occur between the measurement time and the laser treatment time is accounted for. Often times, it is probable that when the patient eye is docked for treatment such as with the suction ring of the patient interface 52, the eye, including its various anatomical features, will change its position relative to the laser system coordinates. This change can be a result of patient head movement, eye movement, or because of force applied during docking. In some cases, the refractive properties of the air or any liquid over the eye can distort the images of the eye. For example, the suction ring of the patient interface 52 may be filled with one or more of a solution, saline, or a viscoelastic fluid. It can be helpful to transform the corneal measurements, like the astigmatic axis angle, to a new coordinate system to account for any movement and distortion. Several means for accomplishing this are provided.

In some embodiments, the operator can mark the patient eye prior to the measurement with ink dots that are typically positioned diametrically across on the periphery of the cornea in a step 578. These dots can be acquired by the imaging camera after docking for treatment and used for calculating the coordinate transformation in a step 581.

In other embodiments, ocular features that are visible in the video images, or in the OCT images or other scans taken during the measurement step are used. These features are correlated to the images taken after docking for treatment in a step 584. This correlation can be performed by digital image processing algorithms, or manually by the operator. When performed manually, the operator is presented by overlapped images (measurement and treatment steps) on the control screen, and the images are manually manipulated in translation and rotation until they are visibly matched. The image manipulation data can be detected by the display software and used for the coordinate transform.

Although the above steps show method 500 of providing accurate and distortion-free corneal topography measurement and subsequent integration with the laser treatment according to many embodiments, a person of ordinary skill in the art will recognize many variations based on the teaching described herein. The steps may be completed in a different order. Steps may be added or deleted. For example, the shape of the cornea may be measures before, during, or after docking for treatment such as with a suction ring of the patient interface 52. Many of the steps may be repeated as often as beneficial to the method.

One or more of the steps of the method 500 may be performed with the circuitry as described herein, for example, one or more the processor or logic circuitry such as the programmable array logic for field programmable gate arrays. The circuitry may be programmed to provide one or more of the steps of method 500, and the program may comprise program instructions stored on a computer readable memory or programmed steps of the logic circuitry such as the programmable array logic or the field programmable gate array, for example.

The blink detection system and method described here are preferably used in connection with one or more of the Positioning Step 525 and Measurement Step 550 in the method 500. Referring to FIG. 2, in the laser eye surgery system 2, the OCT system of the ranging subsystem 46 may be used to position the patient eye in the step 525 and/or to measure the shape of the cornea in the step 550. For the laser eye surgery system 2, the topography measurement structure 53 is used to measure the shape of the cornea in the step 550. The shape of the cornea can be measured before, during, or after the patient interface 52 is docked with the eye of the patient. Images captured by the ranging subsystem 46 of the laser eye surgery system 2 or the imaging subsystem 51 of the laser eye surgery system 2 and the corneal topographer 53 may be displayed with a display of the control panel/GUI 56 of the laser eye surgery system 2 or the display 56A of the laser eye surgery system 2A, respectively. The control panel/GUI 56 may also be used to modify, distort, or transform any of the displayed images.

All patents and patent applications cited here are hereby incorporated by reference hereby reference in their entirety.

Further, the subject matter of the present disclosure is related to the following patent applications: U.S. application Ser. No. 12/048,182, filed Mar. 3, 2008, entitled "METHOD AND APPARATUS FOR CREATING INCISIONS TO IMPROVE INTRAOCULAR LENS PLACEMENT," U.S. application Ser. No. 12/048,186, filed Mar. 13 2008, entitled "METHOD AND APPARATUS FOR CREATING OCULAR SURGICAL AND RELAXING INCISIONS," U.S. application Ser. No. 14/069,703, filed Nov. 1, 2013, entitled "LASER EYE SURGERY SYSTEM CALIBRATION," U.S. application Ser. No. 14/256,307, filed Apr. 18, 2014, entitled "CORNEAL TOPOGRAPHY MEASUREMENT AND ALIGNMENT OF CORNEAL SURGICAL PROCEDURES," U.S. patent application Ser. No. 14/199,087, filed Mar. 6, 2014, entitled "MICROFEMTOTOMY METHODS AND SYSTEMS," U.S. Ser. No. 14/255,430, filed Apr. 17, 2014, entitled "LASER FIDUCIALS FOR ALIGNMENT IN CATARACT SURGERY," and U.S. patent application Ser. No. 14/069,703; filed Nov. 1, 2013, entitled "LASER EYE SURGERY SYSTEM CALIBRATION." The entire disclosures of the above applications are incorporated here by reference, and are suitable for combination with and according to the embodiments disclosed in this application.

The methods and apparatus as described here are suitable for combination with one or more components of laser eye surgery systems that are under development or commercially available such as: the adaptive patient interface is described in Patent Cooperation Treaty Patent Application ("PCT") PCT/US2011/041676, published as WO 2011/163507, entitled "ADAPTIVE PATIENT INTERFACE"; the device and method for aligning an eye with a surgical laser are described in PCT/IB2006/000002, published as WO 2006/09021, entitled "DEVICE AND METHOD FOR ALIGNING AN EYE WITH A SURGICAL LASER"; the device and method for aligning an eye with a surgical laser are described in PCT/IB2006/000002, published as WO 2006/09021, entitled "DEVICE AND METHOD FOR ALIGNING AN EYE WITH A SURGICAL LASER"; the apparatus for coupling an element to the eye is described in U.S. application Ser. No. 12/531,217, published as U.S. Pub. No. 2010/0274228, entitled "APPARATUS FOR COUPLING AN ELEMENT TO THE EYE"; and the servo-controlled docking force device for use in ophthalmic applications is described in U.S. application Ser. No. 13/016,593, published as U.S. Pub. No. US 2011/0190739, entitled "SERVO CONTROLLED DOCKING FORCE DEVICE FOR USE IN OPHTHALMIC APPLICATIONS." The entire disclosures of the above applications are incorporated here by reference and are suitable for combination with and according to the embodiments disclosed in this application.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

The invention claimed is:

1. A laser eye surgical system capable of blink detection, comprising:
a topography measurement structure having at least one geometric marker, the topography measurement structure being configured to be placed into a position proximal to an eye of a patient such that light traveling from the at least one geometric marker is capable of reflecting off a refractive structure of the eye of the patient;
an image capture device configured to detect light reflected from the eye of the patient for a predetermined time period while the topography measurement structure is at the proximal position, and to convert the detected light into image data; and
control electronics coupled to the image capture device and configured to analyze the image data to determine whether light corresponding to the geometric marker is detected in the reflected light, wherein if the light corresponding to the geometric marker is determined not to be present, the control electronics identifies the patient as having blinked during the predetermined time.

2. The laser eye surgical system of claim 1, wherein the at least one geometric marker comprises a circle.

3. The laser eye surgical system of claim 1, wherein there are a plurality of geometric markers, and the geometric markers comprise at least two concentric circles.

4. The laser eye surgical system of claim 3, wherein the plurality of geometric markers are two concentric circles.

5. The laser eye surgical system of claim 1, wherein the refractive structure of the eye is a cornea.

6. The laser eye surgical system of claim 5, wherein the light is reflected off a tear film of the cornea.

7. The laser eye surgical system of claim 1, wherein the control electronics is configured to analyze the image data by performing at least one of a Hough transform of the image data, fitting the image data and measuring a goodness of fit, and image correlation with geometric marker template.

8. The laser eye surgical system of claim 1, wherein the control electronics is configured to analyze the image data by performing a Hough transform of the image data.

9. The laser eye surgical system of claim 1, wherein the image capture device configured is configured to periodically re-detect the light reflected from the refractive structure of the eye.

10. A laser eye surgical system, comprising:
a topography measurement structure having at least one geometric marker, the topography measurement structure being configured to be placed into a position proximal to an eye of a patient such that light traveling from the at least one geometric marker is capable of reflecting off a refractive structure of the eye of the patient;

an optical coherence tomography (OCT) system for generating structural or position data regarding the eye of the patient, the OCT system generating an OCT measurement beam which passes through the topography measurement structure;

an image capture device configured to capture images of reflected light which is reflected from the refractive structure of the eye of the patient to generate image data; and control electronics configured to control the OCT system to generate the structural or position data regarding the eye, to control the image capture device to periodically capture the images during at least a portion of a time when the OCT system generates the structural or position data regarding the eye, and to analyze the image data to determine whether light corresponding to the geometric marker was present in the reflected light, wherein if the light corresponding to the geometric marker is determined not to be present, the control electronics identifies the patient as having blinked during the portion of the time.

11. The laser eye surgical system of claim 10, wherein the control electronics controls the OCT system to re-generate the structural or position information regarding the eye of the patient when it identifies the patient as having blinked during the portion of the time.

12. The laser eye surgical system claim 10, wherein the control electronics identifies that the structural or position data corresponding to the time periods during which the patient has been identified to have blinked are not accurate.

13. The laser eye surgical system of claim 10, wherein the control electronics removes structural or position data corresponding to the time periods during which the patient has been identified to have blinked.

14. The laser eye surgical system of claim 10, wherein the at least one geometric marker comprises a circle.

15. The laser eye surgical system of claim 10, wherein there are a plurality of geometric markers, and the geometric markers comprise at least two concentric circles.

16. The laser eye surgical system of claim 15, wherein the plurality of geometric markers are two concentric circles.

17. The laser eye surgical system of claim 10, wherein the refractive structure of the eye is a cornea.

18. The laser eye surgical system of claim 17, wherein the light is reflected off the tear film of the cornea.

19. The laser eye surgical system of claim 10, wherein the control electronics is configured to analyze the image data by performing at least one of a Hough transform of the image data, fitting the image data and measuring a goodness of fit, and image correlation with geometric marker template.

20. The laser eye surgical system of claim 10, wherein the control electronics is configured to analyze the image data by performing a Hough transform of the image data.

* * * * *